United States Patent
Okano et al.

(10) Patent No.: US 10,029,965 B2
(45) Date of Patent: Jul. 24, 2018

(54) PROCESS FOR PRODUCING POLYHYDRIC ALCOHOL

(71) Applicant: KURARAY CO., LTD., Kurashiki-shi (JP)

(72) Inventors: Shigeru Okano, Kamisu (JP); Kazuyuki Yada, Kamisu (JP); Yutaka Suzuki, Kamisu (JP)

(73) Assignee: KURARAY CO., LTD., Kurashiki-shi (JP)

( * ) Notice: Subject to any disclaimer, the term of this patent is extended or adjusted under 35 U.S.C. 154(b) by 419 days.

(21) Appl. No.: 14/896,210

(22) PCT Filed: Jun. 3, 2014

(86) PCT No.: PCT/JP2014/064741
§ 371 (c)(1),
(2) Date: Dec. 4, 2015

(87) PCT Pub. No.: WO2014/196530
PCT Pub. Date: Nov. 12, 2014

(65) Prior Publication Data
US 2016/0115108 A1    Apr. 28, 2016

(30) Foreign Application Priority Data

Jun. 4, 2013 (JP) .................... 2013-117882

(51) Int. Cl.
*C07C 29/132* (2006.01)
*C07C 29/88* (2006.01)

(52) U.S. Cl.
CPC ............ *C07C 29/132* (2013.01); *C07C 29/88* (2013.01)

(58) Field of Classification Search
CPC ............................... C07C 29/132; C07C 29/88
See application file for complete search history.

(56) References Cited

U.S. PATENT DOCUMENTS

| | | | |
|---|---|---|---|
| 3,966,827 A | 6/1976 | Aquila et al. | |
| 4,091,041 A | 5/1978 | Smith | |
| 4,663,468 A | 5/1987 | Tokitoh et al. | |
| 4,861,922 A | 8/1989 | Tokitoh et al. | |
| 6,137,016 A | 10/2000 | Wood et al. | |
| 7,560,601 B2 * | 7/2009 | Hino ............ | C07C 29/132 568/865 |
| 2009/0099392 A1 | 4/2009 | Hino et al. | |

FOREIGN PATENT DOCUMENTS

| | | |
|---|---|---|
| JP | 50-106910 A | 8/1975 |
| JP | 54-36207 A | 3/1979 |
| JP | 58-167532 A | 10/1983 |
| JP | 60-252438 A | 12/1985 |
| JP | 1-100139 A | 4/1989 |
| JP | 2000-507566 A | 6/2000 |
| WO | 2007/125909 A1 | 11/2007 |

OTHER PUBLICATIONS

International Search Report dated Sep. 2, 2014 in PCT/JP2014/064741 filed Jun. 3, 2014.

\* cited by examiner

*Primary Examiner* — Yate' K Cutliff
(74) *Attorney, Agent, or Firm* — Oblon, McClelland, Maier & Neustadt, L.L.P.

(57) ABSTRACT

A process for producing a polyhydric alcohol includes a step (I) of hydrogenating hemiacetal having a specific structure to obtain a reaction solution (I), and a step (II) of adding water to the reaction solution (I) obtained in the step (I) and further conducting hydrogenation.

4 Claims, No Drawings

PROCESS FOR PRODUCING POLYHYDRIC ALCOHOL

TECHNICAL FIELD

The present invention relates to a process for producing a polyhydric alcohol. In more detail, the invention relates to a process for producing a high purity polyhydric alcohol having small content of impurities in the production of a polyhydric alcohol by reduction of hemiacetal.

BACKGROUND ART

Polyhydric alcohol is utilized as a raw material of a synthetic resin and a surfactant, a high boiling point solvent, and a material of antifreeze. The polyhydric alcohol has excellent moisture retaining property and antibacterial property and has a function to repair a hair cuticle. Therefore, the polyhydric alcohol is widely used as a feeling improver for improving spread and slip of a moisturizing agent and cosmetics.

In such an intended use of the polyhydric alcohol, the polyhydric alcohol having higher purity is desired in order to prevent the problems of coloration, performance deterioration and generation of offensive odor due to contamination of impurities.

Numerous methods are known as a synthesis example of a polyhydric alcohol. As one example, a method of reducing hemiacetal such as 2-hydroxy-4-methyltetra-hydroxypyrane or 2-hydroxytetrahydrofuran is known (see Patent Documents 1 to 5).

In Patent Document 1,3-methylpentane-1,5-diol is synthesized by a hydrogenation reaction of 2-hydroxy-4-methyltetrahydropyrane. In this synthesis, it is known that an acetal compound (hereinafter referred to as "MPAE") represented by the following formula (2) is by-produced.

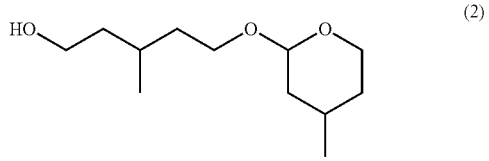
(2)

MPAE has a boiling point close to that of 3-methylpentane-1,5-diol, and is therefore difficult to separate by distillation. This causes decrease of yield from the standpoint of the separation of 3-methylpentane-1,5-diol. For this reason, in conducting a hydrogenation reaction of 2-hydroxy-4-methyltetrahydropyrane, a method of suppressing the amount of MPAE as a by-product by a method of using molybdenum-modified Raney nickel as a hydrogenation catalyst (Patent Document 2) or a method of hydrogenating in the presence of a basic compound (Patent Document 3) is proposed.

Furthermore, it is indicated in Patent Documents 2 and 3 that in a hydrogenation reaction of 2-hydroxy-4-methyltetrahydropyrane, β-methyl-δ-valero-lactone (hereinafter referred to as "MVL") represented by the following formula (3)

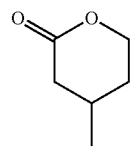
(3)

is by-produced, and a suppression method of its formation is proposed.

On the other hand, in Patent Documents 4 and 5, in order to remove 2-(4-hydroxybutoxy)tetrahydrofuran, which is by-produced in the production of 1,4-butanediol by a hydrogenation reaction of a hydroformylated product (2-hydroxytetrahydrofuran) of allyl alcohol and is difficult to separate from 1,4-butanediol by distillation, a method of conducting hydrogenation in the presence of water is proposed.

PRIOR ART DOCUMENTS

Patent Documents

Patent Document 1: JP-A-50-106910
Patent Document 2: JP-A-1-100139
Patent Document 3: WO 2007/125909
Patent Document 4: JP-A-58-167532
Patent Document 5: JP-T-2000-507566

SUMMARY OF THE INVENTION

Problems that the Invention is to Solve

However, in the method of Patent Document 2, the amount of MPAE as a by-product is 1%, and there is a room for further improvement in the effect of suppressing the formation. In the method of Patent Document 3, a purity of a polyhydric alcohol obtained (3-methylpentane-1,5-diol) was at most 99.1%.

In the method of Patent Document 4, an expensive noble metal catalyst should be used in a hydrogenation reaction. Furthermore, in the method of Patent Document 5, an acetal compound (2-(4-hydroxybutoxy)tetrahydrofuran) can be removed, but there was the problems that a yield of a target substance is decreased by a side-reaction of butanediol and sufficiently high purity is not achieved.

In Patent Documents 2 and 3, it is understood that distillation operation can be continued until non-detection of MVL by distillation, but this requires sufficient distillation facilities, and there is a concern that cost for facilities is increased.

In view of the above, an object of the present invention is to provide a process capable of producing a high purity polyhydric alcohol industrially advantageously in good yield by reduction of hemiacetal.

Means for Solving the Problems

As a result of intensive investigations, the present inventors have succeeded to produce a high purity polyhydric alcohol by adding water to a reaction solution containing a polyhydric alcohol obtained by hydrogenation of hemiacetal having a specific structure, and further performing a reaction under hydrogenation conditions.

That is, the present invention is as follows.

[1] A process for producing a polyhydric alcohol, comprising:
a step (I) of hydrogenating hemiacetal represented by the following formula (1-1) or (1-2) to obtain a reaction solution (I); and
a step (II) of adding water to the reaction solution (I) obtained in the step (I) and further conducting hydrogenation:

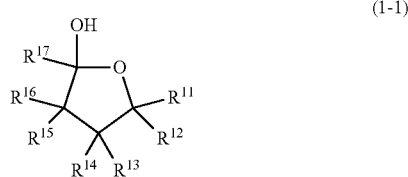

(1-1)

(in the formula (1-1), $R^{11}$ to $R^{17}$ each independently represent a hydrogen atom, an alkyl group or aryl group which may have a functional group, provided that all of $R^{11}$ to $R^{17}$ does not represent a hydrogen atom);

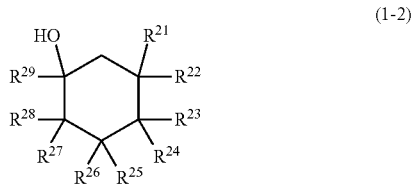

(1-2)

(in the formula (1-2), $R^{21}$ to $R^{29}$ each independently represent a hydrogen atom, an alkyl group or aryl group which may have a functional group.)

[2] The process for producing a polyhydric alcohol as described in [1], wherein an amount of water added in the step (II) is 1 mol times or more based on by-products in the reaction solution (I) and from 20 to 100 mass % based on the reaction solution (I).

[3] The process for producing a polyhydric alcohol as described in [1] or [2], wherein the hydrogenation in the step (II) is conducted in the presence of a hydrogenation catalyst, the hydrogenation catalyst is a heterogeneous catalyst, and a carrier of a metal is selected from silica, alumina and diatomaceous earth.

Advantageous Effects of the Invention

According to a production process of the present invention, a high purity polyhydric alcohol having smaller content of impurities can be produced industrially advantageously in good yield.

MODE FOR CARRYING OUT THE INVENTION

<Step (I)>
Step (I) is a step of hydrogenating hemiacetal (1) to obtain a reaction solution (I).
[Hemiacetal (1)]
Hemiacetal (1) is described.
$R^{11}$ to $R^{17}$ in the formula (1-1) and $R^{21}$ to $R^{29}$ in the formula (1-2) each independently represent a hydrogen atom, an alkyl group or aryl group which may have a functional group. However, in the formula (1-1), all of $R^{11}$ to $R^{17}$ does not represent a hydrogen atom.

As the alkyl group, an alkyl group having from 1 to 8 carbon atoms is preferred, an alkyl group having from 1 to 6 carbon atoms is more preferred, methyl group, ethyl group, propyl group, isopropyl group, butyl group, isobutyl group, s-butyl group, t-butyl group, pentyl group, hexyl group, cyclopentyl group and cyclohexyl group are still more preferred, and methyl group is particularly preferred.

Examples of the aryl group include phenyl group, tolyl group, 1-naphthyl group and 2-naphthyl group.

Examples of the functional group include a hydroxyl group; an ether group such as methoxy group, ethoxy group, propoxy group, butoxy group, isobutoxy group, s-butoxy group, t-butoxy group, cyclopentyloxy group, cyclohexyloxy group, 2-methoxyethoxy group, 2-ethoxyethoxy group, furyl group, tetrahydrofuryl group, tetrahydropyranyl group, phenoxy group, benzyloxy group, biphenyloxy group or naphthyloxy group; a ketone group such as acetyl group or benzoyl group; an aldehyde group such as formyl group; a carboxylic acid group and its metal salt; acyloxy group such as acetoxy group or benzoyloxy group; a carbonic acid ester group such as methoxycarbonyloxy group or phenoxycarbonyloxy group; a cyano group; a sulfide group such as methylsulfanyl group or phenylsulfanyl group; a sulfoxide group such as methylsulfinyl group or phenylsulfinyl group; a sulfonyl group such as methylsulfonyl group or phenylsulfonyl group; sulfonic acid group and its metal salt; a silyl group such as trimethylsilyl group or triphenylsilyl group; a phosphino group such as dimethylphosphino group, dibutylphosphino group or diphenylphosphino group; a phosphine oxide group such as oxodimethylphosphino group, oxodibutylphosphino group or oxodiphenylphosphino group; phosphonic acid group and its metal salt; and a halogen group such as chloro group or bromo group.

In the present invention, 2-hydroxy-4-methyltetrahydrofuran or 2-hydroxy-4-methyltetrahydropyrane is particularly preferred as the hemiacetal (1).
[Hydrogenation in Step (I)]
Hydrogenation of hemiacetal (1) is preferably conducted in the presence of a hydrogenation catalyst.
The hydrogenation catalyst is not particularly limited, and the conventional hydrogenation catalysts can be used. However, a heterogeneous catalyst is preferred from the standpoint of addition of water to the reaction solution (1) in a step (II).
Examples of the heterogeneous catalyst include a palladium catalyst such as palladium/carbon, palladium/alumina or palladium black; a ruthenium catalyst such as ruthenium/carbon, ruthenium/alumina or ruthenium oxide; a platinum catalyst such as platinum/carbon, platinum/alumina or platinum oxide; a rhodium catalyst such as rhodium/carbon or rhodium/alumina; a nickel catalyst such as Raney nickel, nickel/diatomaceous earth, nickel/alumina or nickel/silica; a copper catalyst such as Raney copper; and a cobalt catalyst such as Raney cobalt or cobalt/alumina.
Of those, a nickel catalyst is preferred from the standpoint of reaction result and cost.
Furthermore, a carrier of the metal of the heterogeneous catalyst is preferably selected from silica, alumina and diatomaceous earth.
The hydrogenation catalyst may be used in one kind alone or as mixtures of two or more kinds thereof. The amount of the hydrogenation catalyst used is not always limited, but the hydrogenation catalyst is generally used in an amount of preferably from 0.1 to 10 mass %, and more preferably from 1 to 5 mass %, based on the total amount of the hemiacetal (1) used. When the amount of the hydrogenation catalyst used is 0.1 mass % or more, a reaction proceeds in a sufficient reaction rate, which is advantageous. On the other hand, when the amount is 10 mass % or less, heat generation or runaway reaction due to a rapid reaction can be suppressed, which is advantageous.

The metal of the heterogeneous catalyst may be modified with a different kind of a metal, such as chromium, molybdenum, aluminum or tungsten.

In the present invention, the type of hydrogenation may be a batch type or a continuous type.

In the present invention, a supply method of hydrogen to a reaction system is not particularly limited, but it is preferred that hydrogen is continuously supplied. Hydrogen may be diluted with an inert gas. Furthermore, the reaction pressure in the present invention is not particularly limited, but is preferably from 0.1 to 10 MPa, and more preferably from 0.2 to 2.0 MPa, as hydrogen partial pressure. When the hydrogen partial pressure is 0.1 MPa or higher, sufficient reaction rate is obtained, which is advantageous. When the hydrogen partial pressure is 10 MPa or lower, an expensive reactor having pressure-resistant performance is not required, which is economically advantageous.

The reaction temperature of hydrogenation of the step (I) is not particularly limited. In general, the reaction pressure is preferably a range of from 60 to 180° C., and more preferably from 90 to 150° C. When the reaction temperature is 60° C. or higher, sufficient reaction rate is obtained, which is advantageous, and when the reaction temperature is 180° C. or lower, progress of a side-reaction can be sufficiently suppressed, which is advantageous.

The reaction solution (I) obtained in the step (I) contains by-products such as an acetal compound and a lactone compound, in addition to a polyhydric alcohol which is a target substance of the present invention. The "acetal compound" used in the present description is typically a compound formed by the reaction between a polyhydric alcohol which is an aimed product, and hemiacetal (1), and corresponds to, for example, MFAE in examples and comparative examples described hereinafter, MPAE in the hydrogenation reaction of 2-hydroxy-4-methyltetrahydropyrane, and 2-(4-hydroxybutoxy)tetrahydrofuran in the hydrogenation reaction of a hydroformylated product (2-hydroxytetrahydrofuran) of allyl alcohol. In the present description, the lactone compound is typically a compound formed by partial dehydrogenation of hemiacetal (1) under hydrogenation reaction conditions, and corresponds to, for example, MBL in examples and comparative examples described hereinafter, and MVL in the hydrogenation reaction of 2-hydroxy-4-methyltetrahydropyrane.

<Step (II)>

Step (II) is a step of adding water to the reaction solution (I) obtained in the step (I) and further conducting hydrogenation.

In the step (II), the reaction solution (I) obtained in the step (I) may be directly used, and a solution obtained by once purifying the solution after the step (I) may be used.

[Addition of Water]

In the case of conducting the reaction in a continuous manner, water may be previously mixed with the reaction solution (I) and fed, and the reaction solution (I) and water may be separately fed.

Water may be ordinary water, but pure water or distilled water is more desired. The form of water may be a liquid (water) and may be a gas (water vapor). The gas (water vapor) may be normal pressure water vapor and may be water vapor in a pressurized state.

The amount of water added is determined by the content of the by-products. The amount is preferably 1 mol times or more based on the by-products in the reaction solution (I), and is preferably from 20 to 100 mass %, more preferably from 20 to 90 mass %, and still more preferably from 20 to 80 mass %, based on the reaction solution (I). When the amount of water is 20 mass % or more, sufficient effect appears, an acetal compound and a lactone compound that are difficult to separate by distillation react, and the yield of a polyhydric alcohol increases. Furthermore, formation of an ether form by a dehydration reaction of a polyhydric alcohol does not occur, which is preferred. When the amount of water used is 100 mass % or less, thermal load applied to a reboiler does not become too large, which is preferred.

[Hydrogenation in Step (II)]

The conditions of hydrogenation in the step (II) and specific examples and preferred range of the hydrogenation catalyst are the same as described in the step (I).

By adding water to the reaction solution (I), an acetal compound which is a by-product contained in the reaction solution (I) is hydrolyzed, and a polyhydric alcohol as a target product and hemiacetal as a raw material are formed. By further hydrogenation, a polyhydric alcohol is formed from the hemiacetal as a raw material. By this, the purity of the polyhydric alcohol as a target product can be increased. Furthermore, since the lactone compound is converted into a polyhydric alcohol as a target product by hydrogenation, the purity of the polyhydric alcohol is similarly increased. Furthermore, by the presence of water, a dehydration reaction of a polyhydric alcohol is suppressed, thereby the formation of an ether product is suppressed, and the yield can be maintained high.

In the present invention, use of a solvent is not essential, but a solvent may be used. A material that does not cause a reaction with a raw material and a product and is mixed with a raw material and a product to form a uniform solution is preferred as the solvent, and examples of the solvent include ethers such as tetrahydrofuran and 1,4-dioxane. When the solvent is used, the amount is not particularly limited. However, in general the amount is preferably 100 mass % or less based on the hemiacetal (1). When the amount of the solvent used is 100 mass % or less, such an amount is advantageous from the standpoints of removal of reaction heat, suppression of by-products and suppression of energy required in recovery of a solvent.

Separation of the polyhydric alcohol from the reaction solution obtained can be conducted by ordinary distillation. Distillation column may be a perforated plate column, a bubble cap column or the like. Preferably, when separation purification by vacuum distillation is conducted using a low pressure loss packed column, high purity polyhydric alcohol can be easily obtained.

EXAMPLES

The present invention is specifically described below by reference to examples, but it should be understood that the invention is not construed as being limited to those examples. In the examples, gas chromatography analysis was conducted under the following conditions, and the yield was obtained by an internal standard method by a calibration curve method.

[Gas Chromatography Analysis Condition]

Analytical instrument: GC-2014 (manufactured by Shimadzu Corporation)

Detector: FID (flame ionization detector)

Column used: DB-1 (length: 30 m, membrane thickness: 0.25 μm, inner diameter: 0.25 mm) (manufactured by Agilent Technologies)

Analysis condition: Injection Temp.: 250° C., Detection Temp.: 250° C.

Temperature-rising condition: from 60° C. (holding for 5 min), rising temperature in 5° C./min, to 210° C. (holding for 5 min)

In the following examples and comparative examples, a compound represented by the following formula (4) is referred to as "MTHP".

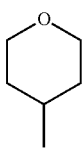
(4)

In the following examples and comparative examples, an acetal compound represented by the following formula (5) and an acetal compound represented by the following formula (6) are collectively referred to as "MFAE".

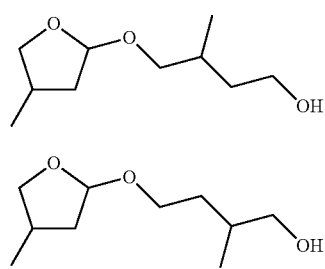
(5)

(6)

In the following examples and comparative examples, a lactone compound represented by the following formula (7) is referred to as "MBL".

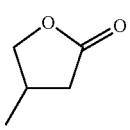
(7)

In the following examples and comparative examples, a compound represented by the following formula (8) is referred to as "MTHF".

(8)

Reference Example 1

A toluene solution (175 mL) obtained by dissolving (acetylacetonato)di-carbonyl rhodium (36.1 mg, 0.14 mmol) and tri(2-tert-butyl-4-methylphenyl)phosphite (11.9 g, 22.8 mmol), and triethylamine (1.0 g) were added to 3-methyl-3-butene-1-ol (3,325 mL, 2,840 g), followed by heating at 80° C. Pressure in a reactor was maintained at 5 MPa with a mixed gas of carbon monoxide:hydrogen=1:1 (molar ratio), and reaction was conducted in an offgas flow rate of 20 L/hr. Conversion of 3-methyl-3-butene-1-ol reached 100% in 6 hours, and a reaction solution obtained was subjected to simple distillation to obtain 2-hydroxy-4-methyltetrahydropyrane having a purity of 96.3% (yield: 92.4%).

Reference Example 2

Reaction was conducted in the same manner as in Reference Example 1, except for using methallyl alcohol (3,325 mL, 2,840 g) in place of 3-methyl-3-butene-1-ol (3,325 g, 2,840 g). The reaction solution obtained was subjected to simple distillation to obtain 2-hydroxy-4-methyltetrahydrofuran having a purity of 90.1% (yield: 88.0%).

Example 1

Step I 0.67 g of 30% sodium hydroxide aqueous solution was added to 2-hydroxy-4-methyltetrahydropyrane (1,000 mL, 855 g) obtained in Reference Example 1, using Raney nickel (BK113AW, manufactured by Evonik Degussa Japan Co., Ltd., 30 g) as a hydrogenation catalyst, and hydrogen was incorporated so as to achieve reaction temperature: 120° C. and reaction pressure: 0.8 MPa. One hour later after the temperature reached 120° C., 2,000 mL of 2-hydroxy-4-methyltetrahydropyrane containing 1.33 g of 30% sodium hydroxide aqueous solution was fed to the reactor over 4 hours. After completion of the feeding, the reaction was conducted by stirring for 2 hours. 2-hydroxy-4-methyltetrahydropyrane was completely consumed, and the reaction solution obtained was subjected to simple distillation, thereby obtaining 1,972 mL of a reaction solution (1-I) containing 3-metylpentane-1,5-diol (92.3%), MPAE (0.2%) and MVL (2.0%).

Step II

Distilled water (440 g) and nickel/diatomaceous earth (N103LK, manufactured by JGC C&C., 47 g) were added to the reaction solution (1-I) (1,130 g) containing 3-methyl-pentane-1,5-diol (92.3%), MPAE (0.2%) and MVL (2.0%), obtained in the step I above, and hydrogenation was conducted using hydrogen so as to achieve 150° C. and 0.8 MPa. Five hours later, the purity of 3-merthylpentane-1,5-doil reached 93.0%, the content of MPAE was less than 0.1%, and the content of MVL was 1.4%. Formation of an ether product (MTHP) by a dehydration reaction was not observed. The yield of 3-metylpentane-1,5-diol was 101% (the reason that the yield exceeds 100% is that 3-methyl-pentane-1,5-diol was formed from MPAE and MVL). This was distilled in a reflux ratio of 1 under 2 Torr using a distillation column having 5 plates packed with HELI PACK No. 2 (manufactured by TO-TOKU Engineering Corporation). As a result, 3-methylpentane-1,5-diol having a purity of 99.7% was obtained in a distillation yield of 95.0%. The content of MPAE, MVL and MTHP was less than 0.1%.

Example 2

The reaction solution (1-I) obtained in Example 1 was subjected to purification by distillation under reduced pressure in a reflux ratio of 6 under 3 Torr using a distillation column having 20 plates packed with HELI PACK No. 2

(manufactured by TO-TOKU Engineering Corporation), and a reaction solution (1-I') was obtained. Distillation yield was 93.0%, and in the reaction solution (1-I'), the purity of 3-methylpentane-1,5-diol was 99.1%, and MPAE was contained in an amount of 0.2%.

Reaction and purification were conducted in the same manners as in the step II of Example 1, except for using the reaction solution (1-I') in place of the reaction solution (1-I).

That is, distilled water (440 g) and nickel/diatomaceous earth (N103LK, manufactured by JGC C&C., 47 g) were added to the reaction solution (1-I') (1,130 g) containing 3-methylpentane-1,5-diol (99.1%) and MPAE (0.2%), and hydrogenation was conducted using hydrogen so as to achieve 150° C. and 0.8 MPa. Five hours later, the purity of 3-merthylpentane-1,5-doil reached 99.6%, and the content of MPAE was less than 0.1%. Formation of an ether product (MTHP) by a dehydration reaction was not observed. The yield of 3-methylpentane-1,5-diol was 100%. This was distilled in a reflux ratio of 1 under 2 Torr using a distillation column having 5 plates packed with HELI PACK No. 2 (manufactured by TO-TOKU Engineering Corporation). As a result, 3-methylpentane-1,5-diol having a purity of 99.8% was obtained in a distillation yield of 95.0%. The content of MPAE was less than 0.1%, and MVL and MTHP were not detected.

Example 3

Reaction and purification were conducted in the same manners as in the step I of Example 1, except for using 2-hydroxy-4-methyltetrahydrofuran obtained in Reference Example 2 in place of 2-hydroxy-4-methyltetrahydropyrane, and 1,985 mL of a reaction solution (3-I) containing 2-methylbutane-1,4-diol (88.0%), MFAE (1.9%) and MBL (0.3%) was obtained.

The reaction solution (3-I) was subjected to purification by distillation under reduced pressure in a reflux ratio of 6 under 3 Torr using a distillation column having 20 plates packed with HELI PACK No. 2 (manufactured by TO-TOKU Engineering Corporation), and a reaction solution (3-I') was obtained. The distillation yield was 92%, and in the reaction solution (3-I'), the purity of 2-methylbutane-1,4-diol was 98.0%, MPAE was contained in an amount of 1.9%, and MBL was contained in an amount of 0.1%.

Reaction was conducted in the same manner as in the step II of Example 1, except for using the reaction liquid (3-I') (1,130 g) containing 2-methylbutane-1,4-diol (98.0%), MFAE (1.9%) and MBL (0.1%) in place of the reaction solution (1-I). As a result, 2-methylbutane-1,4-diol having a purity of 99.8% was obtained in a yield of 102%. The content of MFAE was 0.2% (the reason that the yield exceeds 100% is that 2-methylbutane-1,4-diol was formed from MFAE). Formation of an ether product (MTHF) by a dehydration reaction was not observed. This was distilled in a reflux ratio of 1 under 3 Torr using a distillation column having 5 plates packed with HELI PACK No. 2 (manufactured by TO-TOKU Engineering Corporation). As a result, 2-methylbutane-1,4-diol having a purity of 99.8% was obtained in a distillation yield of 96.0%. The content of MFAE was 0.2%, and MTHF and MBL were not detected.

Example 4

Reaction and purification were conducted in the same manners as in the step I of Example 1, except that sodium hydroxide was not used, and a reaction solution (4-I) containing 3-methylpentane-1,5-diol (90.0%), MPAE (3.6%) and MVL (6.0%) was obtained.

Reaction and purification were conducted in the same manners as in the step II of Example 1, except for using the reaction liquid (4-I) (1,130 g) containing 3-methylpentane-1,5-diol (90.0%), MPAE (3.6%) and MVL (6.0%) in place of the reaction solution (1-I). As a result, 3-methylpentane-1,5-diol having a purity of 99.7% was obtained in a reaction yield of 103% and a distillation yield of 95.0% (the reason that the yield exceeds 100% is that 3-methylpentane-1,5-diol was formed from MPAE and MVL). Formation of an ether product (MTHP) by a dehydration reaction was not observed. The content of MPAE was 0.2%, and MVL and MTHP were not detected.

Example 5

Reaction was conducted in the same manner as in Example 4, except for changing the amount of distilled water to 250 g. As a result, a reaction yield was 98%, and MTHP was contained in an amount of 0.3% as a product newly detected. The reaction solution was purified in the same manner as in Example 4, and 3-methylpentane-1,5-diol having a purity of 99.5% was obtained in a distillation yield of 92.0%. The content of MPAE was 0.2%, and MVL and MTHP were not detected.

Comparative Example 1

The reaction solution (1-I) was subjected to purification by distillation under reduced pressure in a reflux ratio of 6 under 3 Torr using a distillation column having 20 plates packed with HELI PACK No. 2 (manufactured by TO-TOKU Engineering Corporation). As a result, a distillation yield was 93%, a purity of 3-methylpentane-1,5-diol was 99.1%, the content of MPAE was 0.2%, MVL was 0.1%, and MTHP was 0.1%.

Comparative Example 2

The reaction solution (3-I) was subjected to purification by distillation under reduced pressure in a reflux ratio of 6 under 3 Torr using a distillation column having 20 plates packed with HELI PACK No. 2 (manufactured by TO-TOKU Engineering Corporation). As a result, a distillation yield was 92%, the purity of 2-methylbutane-1,4-diol was 98.0%, the content of MFAE was 1.9%, and MTHF was 0.1%. MBL was not detected.

Comparative Example 3

Reaction was conducted in the same manner as in Example 3, except that distilled water was not added. As a result, a reaction yield was 95%, and the purity of 2-methylbutane-1,4-diol was decreased to 95.0%. MTHF was contained in an amount of 3.0% as a by-product newly detected. The content of MFAE was 1.9%. MBL was not detected. This was distilled in a reflux ratio of 1 under 3 Torr using a distillation column having 5 plates packed with HELI PACK No. 2 (manufactured by TO-TOKU Engineering Corporation). As a result, a distillation yield was 95.0%, and the purity of 2-methylbutane-1,4-diol was 97.8%, the content of MFAE was 1.9%, and MTHF was 0.1%.

Example 6

Reaction was conducted in the same manner as in Example 3, except that the amount of distilled water was decreased to 55 g. As a result, a reaction yield was 96%, and the purity of 2-methylbutane-1,4-diol was decreased to 95.5%. MTHF was contained in an amount of 2.5% as a by-product newly detected. The content of MFAE was 1.5%. MBL was not detected. This was distilled in a reflux ratio of 1 under 3 Torr using a distillation column having 5 plates packed with HELI PACK No. 2 (manufactured by TO-TOKU Engineering Corporation). As a result, a distillation yield was 95.0%, the purity of 2-methylbutane-1,4-diol was 98.4%, the content of MFAE was 1.5%, and MTHF was less than 0.1%.

Example 7

Reaction was conducted in the same manner as in Example 3, except that the amount of distilled water was decreased to 110 g. As a result, a reaction yield was 97%, and the purity of 2-methylbutane-1,4-diol was decreased to 96.2%. MTHF was contained in an amount of 1.8% as a by-product newly detected. The content of MFAE was 1.2%. MVL was not detected. This was distilled in a reflux ratio of 1 under 3 Torr using a distillation column having 5 plates packed with HELI PACK No. 2 (manufactured by TO-TOKU Engineering Corporation). As a result, a distillation yield was 95.0%, the purity of 2-methylbutane-1,4-diol was 98.7%, the content of MFAE was 1.2%, and MTHF was less than 0.1%.

Comparative Example 4

Distilled water (250 g) and nickel/diatomaceous earth (N103LK, manufactured by JGC C&C., 47 g) as a hydrogenation catalyst were added to 2-hydroxy-4-methyltetrahydropyrane (1,000 mL, 855 g) obtained in Reference Example 1, and hydrogen was incorporated so as to achieve a reaction temperature of 120° C. and a reaction pressure of 0.8 MPa. One hour later after the temperature reached 120° C., 2,000 mL of 2-hydroxy-4-methyltetrahydropyrane containing 500 g of distilled water was fed to the reactor over 4 hours. After completion of the feeding, reaction was conducted by stirring for 2 hours. 2-hydroxy-4-methyltetrahydropyrane was completely consumed. The reaction solution obtained was subjected to simple distillation. As a result, 1,950 mL of a reaction solution (6-I) containing 3-metylpentane-1,5-diol (78.3%), MTHP (3.0%), MPAE (10.2%) and MVL (3.0%) was obtained.

INDUSTRIAL APPLICABILITY

The polyhydric alcohol obtained by the production process of the present invention can be widely utilized in a use requiring a high purity product out of a raw material of a synthetic resin and a surfactant, a high boiling point solvent, a material of an antifreezing solution, and a feeling improver for improving spread and slip of a moisturizing agent and cosmetics.

Although the present invention has been described in detail and by reference to the specific embodiments, it is apparent to one skilled in the art that various modifications or changes can be made without departing the spirit and scope of the present invention.

This application is based on Japanese Patent Application No. 2013-117882 filed Jun. 4, 2013, the content of which is incorporated herein by reference.

The invention claimed is:

1. A process for producing a polyhydric alcohol, comprising:
   (I) hydrogenating a hemiacetal represented by a formula (1-1) or (1-2) to obtain a reaction solution; and
   (II) adding water to the reaction solution obtained in (I) and further conducting a hydrogenation:

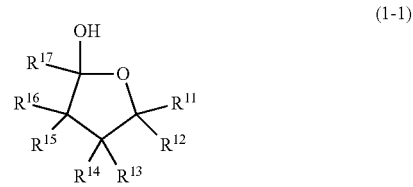

(1-1)

wherein $R^{11}$ to $R^{17}$ each independently represent a hydrogen atom, an alkyl group or aryl group which may have a functional group, provided that not all of $R^{11}$ to $R^{17}$ represent a hydrogen atom;

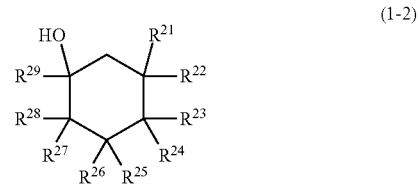

(1-2)

wherein $R^{21}$ to $R^{29}$ each independently represent a hydrogen atom, an alkyl group or aryl group which may have a functional group.

2. The process of claim 1, wherein an amount of water added in (II) is 1 mol times or more based on by-products in the reaction solution and from 20 to 100 mass % based on the reaction solution.

3. The process of claim 1, wherein the hydrogenation in (II) is conducted in the presence of a hydrogenation catalyst, the hydrogenation catalyst is a heterogeneous catalyst, and a carrier of a metal is selected from the group consisting of silica, alumina and diatomaceous earth.

4. The process of claim 2, wherein the hydrogenation in (II) is conducted in the presence of a hydrogenation catalyst, the hydrogenation catalyst is a heterogeneous catalyst, and a carrier of a metal is selected from the group consisting of silica, alumina and diatomaceous earth.

* * * * *